(12) United States Patent
Schuberth et al.

(10) Patent No.: US 11,998,434 B2
(45) Date of Patent: Jun. 4, 2024

(54) ABSORBENT CORE COVER FOR SUPER-ABSORBING ABSORBENT CORES OF SANITARY PRODUCTS

(71) Applicant: Sandler AG, Schwarzenbach (DE)

(72) Inventors: Martin Schuberth, Stammbach (DE); Uwe Bernhuber, Hof (DE)

(73) Assignee: Sandler AG, Schwarzenbach (DE)

( * ) Notice: Subject to any disclaimer, the term of this patent is extended or adjusted under 35 U.S.C. 154(b) by 249 days.

(21) Appl. No.: 17/369,181

(22) Filed: Jul. 7, 2021

(65) Prior Publication Data
US 2022/0023116 A1 Jan. 27, 2022

(30) Foreign Application Priority Data
Jul. 24, 2020 (EP) .................................. 20187625

(51) Int. Cl.
*A61F 13/539* (2006.01)
*A61F 13/15* (2006.01)
(Continued)

(52) U.S. Cl.
CPC ...... *A61F 13/539* (2013.01); *A61F 13/15203* (2013.01); *A61F 13/15731* (2013.01);
(Continued)

(58) Field of Classification Search
CPC ............ A61F 2013/5349; A61F 13/539; A61F 13/15203; A61F 13/15731; A61F 13/536;
(Continued)

(56) References Cited

U.S. PATENT DOCUMENTS 5,701,643 A * 12/1997 Fleissner ................ D04H 18/04
28/105
2015/0173968 A1 6/2015 Joseph
(Continued)

FOREIGN PATENT DOCUMENTS

| DE | 112014002017 T5 | 1/2016 | |
| EP | 3338749 A1 | 6/2018 | |
| WO | WO-2015055177 A1 * | 4/2015 | ............... B32B 3/28 |

OTHER PUBLICATIONS

European Extended Search Report dated Feb. 12, 2021, issued in Application No. EP 20187625.7.

*Primary Examiner* — Susan S Su
(74) *Attorney, Agent, or Firm* — Fox Rothschild LLP (57) ABSTRACT

The present invention relates to an absorbent core for sanitary products with an absorption matrix which comprises a high proportion of super-absorbing particles, and an absorbent core cover for enveloping the absorption matrix, wherein the absorbent core cover comprises at least one upper side sheet and one bottom side sheet, and the absorbent core cover comprises at least one connection region spaced apart from the edge of the absorbent core in which the upper side sheet and the bottom side sheet are connected to each other. Here, at least the upper side sheet of the absorbent core cover is embodied as a fleece composite with a fixing layer with a low permeability to retain the particles in the absorption matrix, and a transfer layer for acquiring fluid. Moreover, the invention relates to a sanitary product having such an absorbent core, the use of a fleece composite as an absorbent core cover, and a method for manufacturing a fleece composite for the upper side sheet of the absorbent core cover.

18 Claims, 3 Drawing Sheets

(51) Int. Cl.
*A61F 13/534* (2006.01)
*A61F 13/536* (2006.01)
*A61L 15/28* (2006.01)
*A61F 13/53* (2006.01)

(52) U.S. Cl.
CPC ............ *A61F 13/536* (2013.01); *A61L 15/28* (2013.01); *A61F 2013/15487* (2013.01); *A61F 2013/15552* (2013.01); *A61F 2013/15959* (2013.01); *A61F 2013/15967* (2013.01); *A61F 2013/530379* (2013.01); *A61F 2013/530489* (2013.01); *A61F 2013/5349* (2013.01)

(58) Field of Classification Search
CPC .. A61F 2013/15487; A61F 2013/15552; A61F 2013/15959; A61F 2013/15967; A61F 2013/530379; A61F 2013/530489; A61L 15/28
See application file for complete search history.

(56) References Cited

U.S. PATENT DOCUMENTS

2016/0074249 A1* 3/2016 Rosati ............... A61F 13/51394
 604/378
2016/0235604 A1* 8/2016 Ehrnsperger ............ A61F 13/53

* cited by examiner

ABSORBENT CORE COVER FOR SUPER-ABSORBING ABSORBENT CORES OF SANITARY PRODUCTS

CROSS-REFERENCE TO RELATED APPLICATIONS

This application claims priority to European Patent Application No. 20187625.7, filed Jul. 24, 2020, the disclosure of which is hereby incorporated by reference in its entirety.

FIELD

The present invention relates generally to an absorbent core for sanitary products.

BACKGROUND

Sanitary products having super-absorbing absorbent cores for acquiring and storing body fluids, for example, baby's napkins, pantiliners, sanitary pads, or incontinence underwear, should permit a preferably high storage volume for the body fluids to be acquired with a preferably small thickness of the overall structure. The body fluid should be removed from the skin as quickly as possible to avoid irritations of the skin and give the wearer a safe and comfortable feeling. To this end, such sanitary products typically comprise a plurality of layers or sheets which provide various functions and are matched to each other. Usually, such sanitary products consist of a top sheet facing the skin and taking care of a quick acquisition and passing-on of the body fluid, an acquisition-distribution layer (ADL) for quickly acquiring and distributing the impinging fluid across the total surface of the sanitary product, an absorbent core for absorbing and immobilizing the body fluid, and a liquid-tight back sheet for preventing a leakage of the body fluid from the sanitary product.

An essential function of the absorbent core is, apart from the absorption and immobilization of the acquired amount of fluid, to keep the latter within the absorbent core for an extended period and to minimize rewetting. Many commercially available sanitary products comprise an absorbent core with an absorption matrix consisting of a mixture of comminuted cellulose and super-absorbing particles (SAP—superabsorber polymer) and which is received in an absorbent core cover. The absorbent core cover consists of an upper side sheet facing the acquisition-distribution layer through which at least the majority of the body fluid penetrates into the absorbent core, and a bottom side sheet facing the optional back sheet. The absorbent core cover serves, apart from receiving the absorption matrix, also for a preferably uniform distribution of the absorption matrix within the absorbent core, and for the absorption matrix remaining in place within the absorbent core. The absorbent core covers known from prior art for encapsulating the absorption matrix with super-absorbing particles usually consist of a thin very fine bonded web with a low permeability with respect to the super-absorbing particles, for example of a simple spunbond, a meltblown fleece, or an SMS fleece (spunbond-meltblown-spunbond) which is manufactured from a combination of the spunbonding and meltblowing methods and is solidified thermally by means of calendars. The bonded webs for the manufacture of a conventional absorbent core cover usually consist of thermoplastic polymers.

To reduce the thickness of the absorbent core and thus improve the wearing comfort for the wearer, there is a tendency in prior art to increase the proportion of super-absorbing particles within the absorption matrix compared to other ingredients, in particular cellulose particles, where absorbent cores exclusively with super-absorbing particles are also suggested. Absorbent cores having a high proportion of super-absorbing particles, however, have a tendency that the body fluid entering the absorbent core of the sanitary product is only bound in a locally restricted manner, whereby a high amount of fluid is distributed to a relatively small surface, and only the super-absorbing particles located within the region of this surface are activated for binding fluids. The super-absorbing particles located outside this surface, however, remain unused. Thereby, the super-absorbing particles wetted by the fluid are very quickly made to swell, a gel coat forming in the outer zone of the absorbent core, which prevents the penetration of further body fluid into the interior of the absorbent core. This condition referred to as "gel blocking" prevents a good acquisition of further spontaneously occurring amounts of fluid. The higher the proportion of super-absorbing particles is within an absorption matrix, the higher is the risk of such gel blocking. It is therefore tried in prior art, in sanitary products having absorbent cores with a high proportion of super-absorbing particles, to distribute a spontaneously occurring high amount of fluid to a preferably large area before the body fluid penetrates into the absorbent core, by means of the acquisition-distribution layer and further optional intermediate layers before the acquisition by the absorbent core.

To avoid or evade gel blocking, or to improve the acquisition and distribution of the body fluids penetrating into the absorbent core, in particular, if the absorbent core has already swelled partially, it is known to divide the absorbent core into several regions by channels, the channels discharging fluid above the absorbent core from already blocked regions into regions having a good absorption capacity. From EP 2 717 823 A1, for example, an absorbent core for sanitary products with two channels essentially extending in the longitudinal direction, which are present both in a dry and in a wet state is known. As soon as the absorbent core absorbs fluid and swells, the channels of the absorbent core assume a three-dimensional shape. Sanitary products with channels permit an improved fit and an improved fluid acquisition and fluid transport during the complete utilization of the sanitary product. From EP 1827335 A1, a further sanitary product is known in which the absorbent core comprises a high proportion of super-absorbing particles and in which the absorbent core cover is provided with a plurality of grooves or guides by which the fluid acquisition of the absorbent core is improved.

Absorbent cores for sanitary products which form, at least in a wet or swelled state of the absorbing absorbent core, three-dimensional channels between the upper side of the absorbent core and a layer disposed above it, for example, the acquisition-distribution layer, can, despite the small thickness of the absorbent core and its flat structure, transport higher amounts of penetrating body fluids more quickly from the surface of the sanitary product and absorb them. In the process, the amount of fluid is not immediately immobilized within the absorbent core, but moves, depending on the position of the sanitary product, in the three-dimensional channel structures. In particular, in case of a lateral lying position, the unbound fluid follows gravity in the channels, which can lead, in an already partially swelled state of the absorbent core, to a leakage of the sanitary product.

Thus, there remains a need to improve the acquisition of the body fluid within the absorbent core of a sanitary product and to reduce a movement of unbound body fluid in channels at the upper side of the absorbent core.

SUMMARY

In one aspect, this disclosure provides an absorbent core for sanitary products having an absorption matrix comprising a high proportion of super-absorbing particles, and an absorbent core cover four enveloping the absorption matrix. The absorbent core cover comprises at least one upper side sheet and one bottom side sheet. The absorbent core cover further comprises at least one connection region spaced apart from the edge of the absorbent core, wherein the upper side sheet and the bottom side sheet are connected to each other.

Also provided in this disclosure includes (a) a sanitary product having an absorbent core described herein, (b) the use of a fleece composite as an absorbent core cover, and (c) a method for manufacturing a fleece composite for the upper side sheet of the absorbent core cover.

DETAILED DESCRIPTION

This disclosure provides an absorbent core for sanitary products having an absorption matrix comprising a high proportion of super-absorbing particles, and an absorbent core cover four enveloping the absorption matrix. The absorbent core cover comprises at least one upper side sheet and one bottom side sheet. The absorbent core cover further comprises at least one connection region spaced apart from the edge of the absorbent core, wherein the upper side sheet and the bottom side sheet are connected to each other.

In some embodiments, at least the upper side sheet of the absorbent core cover is formed, for a generic absorbent core, as a fleece composite having a fixing layer with a low permeability to retain the particles within the absorption matrix, and a transfer layer for acquiring fluid. In the absorbent core for sanitary products according to the invention, in particular for baby's napkins and incontinence underwear, the actual function of the absorbent core cover, the encapsulation of the absorption matrix and the passing-through of the fluid into the absorbent core, is expanded by the functions of an improved fluid absorption, fluid storage, and fluid passage. This is achieved by the use of a fleece composite for the absorbent core cover, wherein not only the upper side sheet facing the acquisition-distribution layer, or the wearer's skin, respectively, but also the bottom side sheet facing away can be designed as a fleece composite.

In some embodiments, the fleece composite has a fixing layer with a low permeability towards the super-absorbing particles and further particles of the absorption matrix to retain the particles within the absorption matrix and to encapsulate the absorption matrix itself within the absorbent core. The absorption matrix of the absorbent core contains, apart from a high proportion of super-absorbing particles, usually also hydrophilic cellulose fibres and optionally also absorbing gelling materials, so that the fluid entering the absorbent core can be quickly bound even in case of a high volume of fluid.

In some embodiments, the proportion of the super-absorbing particles in the absorption matrix is at least 35%, in particular at least 80%, and optionally up to 100%. The upper side sheet and the bottom side sheet of the absorbent core cover are connected to each other at the edge of the absorbent core to ensure the encapsulation of the absorbent core, but are also connected to each other in at least one connection region spaced apart from the absorbent core, for example by means of an adhesive or thermally, so that an indentation is formed in this region compared to the remaining absorbent core. With an oblong shape of the indentation region, a channel is formed on the absorbent core, at least if the absorption matrix has partly swelled by the absorption of fluid, which channel is suited for passing on the unbound fluid in a not swelled region of the absorbent core.

An advantageous embodiment provides for the fixing layer to be embodied as a spunbond or a meltblown, in particular as an SMS fleece (spunbond-meltblown spunbond) with an SMS layer structure, and/or for the transfer layer to be embodied as a staple fibre fleece. An SMS fleece having a typical layer structure wherein a meltblown layer is disposed in the middle between the two spunbonds and is in particular connected to the two spunbond layers by calendar bonding, is, as is known from prior art, very well suited for encapsulating the particles in the absorption matrix with its low air permeability. In some embodiments, an SMS fleece employed as a fixing layer has a grammage of 10 g/m$^2$, in particular of 8 g/m$^2$. As an alternative, the fixing layer can also be embodied as a simple spunbond with a good strength for encapsulating the absorption matrix, or as a meltblown fleece. The staple fibre fleece employed as the transfer layer permits a good acquisition and distribution of fluid and may thus improve the distribution of fluid across the complete absorbent core. Thereby, despite a good encapsulation of the absorption matrix, the complete surface at least of the upper side sheet of the absorbent core cover can be used for the fluid transfer into the absorbent core.

A modification provides for the staple fibres of the staple fibre fleece to be embodied as fine fibres with fibre finenesses within a range of 1.0 to 3.3 dtex, preferably within a range of 1.3 to 2.2 dtex, and a cellulosic fibre proportion of 50% to 100%. The staple fibres of the staple fibre fleece embodied as fine fibres permit a highly improved fluid absorption as well as a good intermediate storage and passing-on of the fluid through the fleece composite to the absorption matrix.

A further embodiment provides for the staple fibres of the staple fibre fleece to be embodied as coarse fibres with fibre finenesses within a range of 3.3 to 12.0 dtex, and a cellulosic fibre proportion of up to 45%, e.g., between 15% and 20%. Such a coarse fibre structure of the staple fibre fleece offers a very high free volume per square meter of the area of the staple fibre fleece, whereby a very high fluid acquisition is achieved temporarily. Due to the reduced proportion of cellulosic fibres, a high proportion of the absorbed amount of fluid can immediately be passed on into the absorption matrix of the absorbent core.

A particular embodiment provides for the staple fibres of the staple fibre fleece to be embodied as a combination of fine fibres and coarse fibres, the fine fibres comprising fibre finenesses within a range of 1.0 to 3.0 dtex and a cellulosic fibre proportion of 50% to 100%, and the coarse fibres comprising fibre finenesses within a range of 3.3 to 12.0 dtex and a cellulosic fibre proportion of up to 45%, e.g., between 15% to 20%. A staple fibre fleece with a combination of fine fibres and coarse fibres permits a high fluid acquisition of the staple fibre fleece on the body's side to be supported by the high capillary fluid absorption over the fine fibres and the high free volume of the coarse fibres. Here, a fixing layer of an SMS fleece facing the absorption matrix can support the dewatering of the needled-in fine fibre fleece towards the absorbent core, resulting in a particularly quick and large-surface distribution of the fluid within the absorbent core. In the application of such a staple fibre fleece within a fleece composite for the upper side sheet of an absorbent core cover four sanitary products, the fine fibres are arranged on the side of the fixing layer, and the coarse fibres are facing the skin of a wearer of the sanitary product.

In some embodiments, the staple fibre fleece can be manufactured by means of a spunlace process. In the spunlace process, water jets are blasted onto a fibre web at high pressure to compact the forming staple fibre fleece. The water jets ejecting from the nozzles with very small diameters at a high pressure lead to the staple fibres of the staple fibre fleece connecting with each other and being solidified. In the process, the capillaries forming in the staple fibre fleece by the water jet process additionally have an advantageous effect on a continuous fluid acquisition towards the absorbent core without hindering the original absorption properties of the staple fibre fleece. By the spunlace process, an increased pore volume can be realised in the staple fibre fleece.

An advantageous embodiment provides for the staple fibre fleece to be needled into a pre-solidified SMS fleece used as a fixing fleece. The needling of the staple fibre fleece with a pre-solidified SMS fleece used as a fixing fleece is a simple and safe mechanical fleece solidification for connecting the two fleece layers. In the process, the incorporation of the staple fibres into the SMS fleece can minimize the interface effects between the SMS fleece and the staple fibre fleece and improve the fluid transfer between the two fleeces.

in some embodiments, the staple fibre fleece can have a fibre surface of greater than 10 $m^2$, e.g., of greater than 12 $m^2$, per 1 $m^2$ of the surface of the staple fibre fleece when the fleece surface is lying level. Depending on the fleece surface one can say that the larger the fibre surface of the staple fibre fleece is in the surface of the absorbent core cover facing away from the absorbent core, the higher is the existing porosity for acquiring fluid in the staple fibre fleece when the fibre finenesses are the same. Furthermore, by means of the size of the fibre surface in the staple fibre fleece, a distinction can be made between fine fibre fleeces and coarse fibre fleeces.

One embodiment provides for the staple fibre fleece of the upper side sheet to comprise a free volume of more than 300,000 $mm^3$, preferably more than 450,000 $mm^3$, per 1 $m^2$ of the surface when the fleece surface is lying level. The free volume of the staple fibre fleece at the surface of the absorbent core cover facing away from the absorbent core is the measure for the existing porosity of the staple fibre fleece. The higher the free volume within the staple fibre fleece is, the more fluid can be acquired by and stored in the fleece.

An advantageous embodiment provides for at least the upper side sheet of the absorbent core cavity to have a thickness of greater than 0.35 mm, e.g., a thickness between 0.5 mm and 1.2 mm. As the thickness of the upper side sheet increases, the free volume or the existing porosity in the upper side sheet of the absorbent core cover will also increase with the volume of the upper side sheet, and thus also the capacity of acquiring fluids and distributing them to the absorption matrix in the absorbent core will increase.

For a safe encapsulation of the absorption matrix by the absorbent core cover, at least the upper side sheet of the absorbent core cover can comprise an air permeability, at a test pressure of 200 Pa, of maximally 3,500 $l/m^2/s$, e.g., of maximally 3,000 $l/m^2/s$. The air permeability is the typical value for assessing the tightness of fleece fabrics, here the upper side sheet of the absorbent core cover, which has to have a sufficient tightness for preventing the leakage of super-absorbing particles.

In a suitable form, at least the upper side sheet of the absorbent core cover can comprise, in a wicking test, a capillary rise of water of at least 10 mm, in particular at least 20 mm, after 300 seconds. The determination of the capillary rise of water in a wicking test describes the soaking behavior of fluids against gravity invoked by the capillary forces in the fleece. The higher the rise of water is, the greater are capillary forces generated in capillary channels in the fleece and the corresponding wicking for the fluid present outside the upper side sheet of the absorbent core cover. High capillary forces permit a good fluid acquisition and distribution in the upper side sheet, wherein the capillary forces differ in response to the wetting properties of the fibre surface and the size of the capillaries with the same capillary rise of water.

In some embodiments, at least the upper side sheet of the absorbent core cover can comprise a total pore volume of at least 0.90 (90 Vol.-%), in particular of 0.925 (92.5 Vol.-%). A high total pore volume permits a high maximum water acquisition. Here, the maximum water acquisition at least of the upper side sheet of the absorbent core cover can be greater than 7 g/g of the upper side sheet, e.g., between 7 g/g and 12 g/g, or greater than 300 $ml/m^2$ of the upper side sheet, e.g., between 300 $ml/m^2$ and 800 $ml/m^2$. The higher the maximum water acquisition of the upper side sheet is, the higher is the fluid amount that can be absorbed by the upper side sheet without compressive load. Here, the indication of the amount of fluid that can be absorbed per area of the upper side sheet is a good assessment for the amount of fluid that can be acquired by the upper side sheet and immobilized.

In a particular embodiment, the run-off proportion for at least the upper side sheet of the absorbent core cover can be smaller than 50% in a run-off test based on WSP 80.9. WSP 80.9 is a standard of the EDANA (European Disposables and Nonwovens Associations). In a run-off test performed based on WSP 80.9, within 4±0.1 seconds, 25 ml of a 0.9% NaCl solution is applied onto the upper side sheet of the absorbent core cover, wherein the upper side sheet is disposed, in contrast to an official run-off test according to WSP 80.9, at an angle of 30°, and not at an angle of 25°. This means that the results achieved in this run-off test based on WSP 80.9 can be better assessed than those of a test according to WSP 80.9. The run-off test permits a statement about the capability of the upper side sheet, to pass on a defined amount of a urine substitute fluid to the underlying layer, while the inclined position of the sanitary product is simulated by the experimental arrangement. The lower the percentage value is, the better is the acquisition or passing-on of the fluid into the upper side sheet and into the underlying absorption matrix of the absorbent core. Furthermore, in this test, the absolute amount of the urine substitute fluid not absorbed by the upper side sheet should be as small as possible since the urine substitute fluid not absorbed by the upper side sheet or the absorption matrix can lead, in a sanitary product as unbound fluid, to a leaking of the sanitary product.

Advantageously, the strike-through time for at least the upper side sheet of the absorbent core cover can be smaller than 3 seconds, e.g., smaller than 1.5 seconds in a strike-through test. In a strike-through test, a defined amount of fluid is selectively introduced into the upper side sheet of the absorbent core cover, and the time until the amount of fluid has been acquired by the upper side sheet, e.g., the staple fibre fleece of the transfer layer, is measured. The shorter the strike-through time is, the better does the acquisition of fluid into the upper side sheet function.

Furthermore, the present invention relates to a sanitary product having an optional top sheet, an acquisition-distribution layer (ADL), an absorbent core for sanitary products according to one of the above-described embodiments, and an optional back sheet, wherein the absorbent core comprises an absorbent core cover with an upper side sheet and a bottom side sheet comprising at least one region spaced apart from the edge of the absorbent core in which the upper side sheet and the bottom side sheet are connected to each other and which forms a usually oblong channel opposite the acquisition-distribution layer when the absorption matrix swells due to the acquisition of fluid. Such a sanitary product permits an improved fluid acquisition of the free fluid present in the channels between the absorbent core cover and the acquisition-distribution layer, and its distribution in the absorbent core. Thereby, in sanitary products with modern absorbent cores, of which the absorption matrix comprises a high proportion of super-absorbing particles and which form, in the swelled state, channels opposite the acquisition-distribution layer, a leakage of the sanitary product is prevented.

Moreover, the invention relates to the use of a fleece composite having a fixing layer and a transfer layer as an absorbent core cover of an absorbent core for sanitary products, in particular for the upper side sheet facing the skin of a wearer, wherein the absorbent core comprises an absorption matrix with a high proportion of super-absorbing particles, wherein the absorbent core cover is embodied for enveloping the absorption matrix, the fixing layer has a low permeability to retain the particles within the absorption matrix, and the transfer layer is suited for acquiring fluid. Such a fleece composite as an absorbent core cover improves the acquisition of fluid and its distribution in the absorbent core, in particular with an already partly swelled absorption matrix.

Furthermore, the invention relates to a method for manufacturing a fleece composite for an upper side sheet of an absorbent core cover of an absorbent core for sanitary products, having a fixing layer of a pre-solidified SMS fleece and a transfer layer of staple fibres, wherein the transfer layer of staple fibres is needled into the pre-solidified SMS fleece. In some embodiments, the transfer layer can be embodied as a staple fibre fleece which is manufactured by means of a spunlace process.

Figure 1:
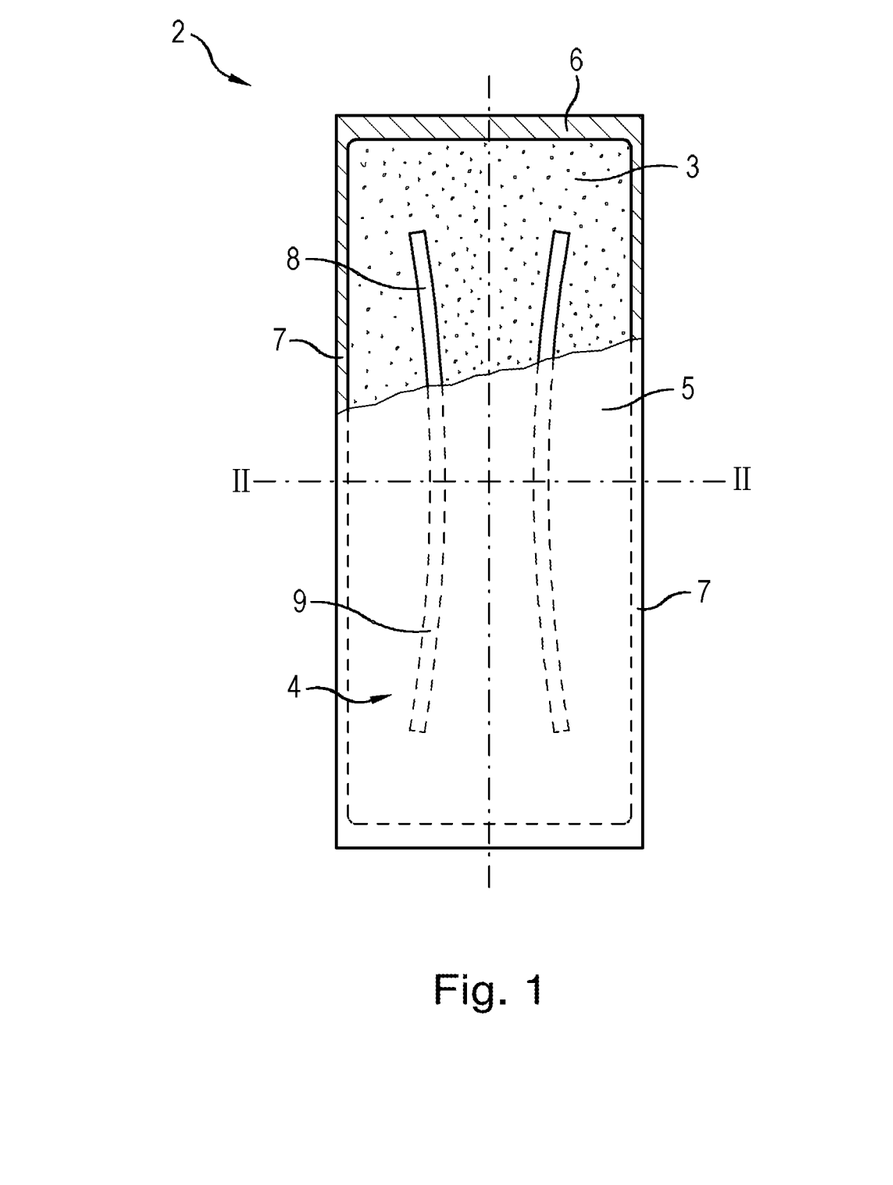
FIG. 1 shows a plan view onto an absorbent core for sanitary products according to the invention.

The exemplary absorbent core 2 for a sanitary product 1 schematically represented in FIG. 1, such as, for example, a baby's napkin, pantiliners, sanitary pads, or incontinence underwear, comprises an absorption matrix 3 of super-absorbing particles (SAP) and optionally further particles, such as, for example, cellulose or gelling agents, and an absorbent core cover 4 enclosing the absorption matrix 3. The absorbent core cover 4 consists of an upper side sheet 5 and a bottom side sheet 6 surrounding the absorption matrix 3 on both sides and being connected to each other at the edge 7 of the absorption matrix 3, for example, by gluing or by means of a thermal bonding method. The absorbent core cover 4 serves, apart from for the encapsulation of the absorption matrix 3, i. e. the prevention of a passage of the particles of the absorption matrix 3 through the absorbent core cover 4, for the transport of fluids through the absorbent core cover 4 into the absorption matrix 3. In the embodiment of the absorbent core 2 according to the invention, the absorbent core cover 4 permits, apart from an essentially vertical transfer of the fluid through the absorbent core cover 4 into the absorption matrix 3, in addition, an improved fluid absorption, a storage of the fluid in the absorbent core cover 4, and the passing-on of the fluid within the absorbent core cover 4 into other regions of the absorbent core 2. The upper side sheet 5 of the absorbent core cover 4 is facing the skin of a wearer.

The absorbent core 2 furthermore comprises at least one connection region 8 spaced apart from the edge 7 of the absorbent core 2 in which the upper side sheet 5 and the bottom side sheet 6 of the absorbent core cover 4 are connected to each other, for example by means of a thermal method or an adhesive. In this connection region 8, in the region of the absorption matrix 3 between the upper side sheet 5 and the bottom side sheet 6, essentially no absorbing particles of the absorption matrix 3, or essentially only inactivated particles of the absorption matrix 3, are present, so that one or more channels 9 are formed in the connection region 8 opposite the remaining absorbent core 2. These channels 9 serve to distribute a fluid entering the sanitary product 1 along the length of the channels 9 across the absorbent core 2.

Figure 2:
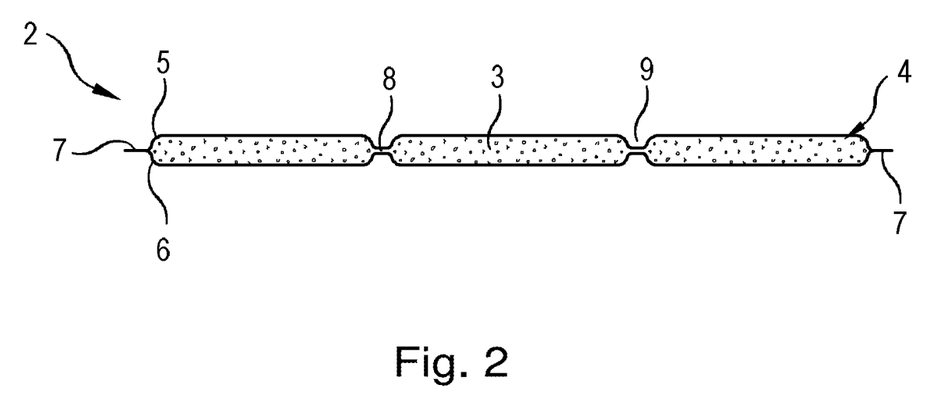
FIG. 2 shows a section through the absorbent core of FIG. 1 along line II-II.

FIG. 2 shows a section through the absorbent core 2 according to the invention of FIG. 1 along line II-II. Apart from the upper side sheet 5 and the bottom side sheet 6 of the absorbent core cover 4 connected to each other at the edge of the absorbent core 2, here, the connection regions 8 between the upper side sheet 5 and the bottom side sheet 6 can be clearly seen at a distance to the edge 7 of the absorbent core cover 4.

Figure 3:
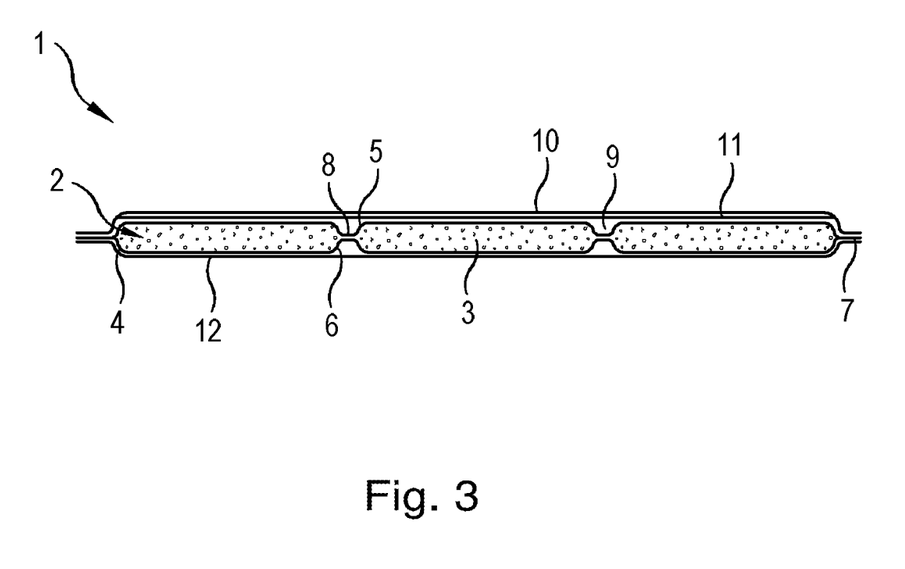
FIG. 3 shows a section through a sanitary product with an absorbent core according to the invention according to FIG. 1 and FIG. 2.

The sectional view through an inventive sanitary product 1 in FIG. 3 shows the arrangement of the absorbent core 2 shown in FIGS. 1 and 2 in a sanitary product 1, for example, in baby's napkins, pantiliners, sanitary pads, or incontinence underwear. This sanitary product 1 comprises an optional top sheet 10 which is in direct contact with the wearer's skin. In some embodiments, the top sheet 10 is yielding, soft and not irritating for the wearer's skin. The top sheet 10 is particularly permeable to fluids, so that body fluid can easily penetrate the top sheet 10. Between the top sheet 10 and the absorbent core 2, furthermore, an acquisition-distribution layer 11 (ADL) is provided which serves to quickly acquire and transfer the occurring fluid to the absorbent core 2. The acquisition-distribution layer 11 creates a distance between the absorbent core 2 and the top sheet 10 and thus further reduces the risks of a rewetting to the wearer. As a bottom termination of the sanitary product 1, a back sheet 12 is provided. The back sheet 12 usually consists of a water-tight material which can be embodied to be breathable and steam-tight. The absorbent core 2 is here positioned between the back sheet 12 and the acquisition-distribution layer 11, the bottom side sheet 6 of the absorbent core cover 4 being positioned towards the back sheet 12. The back sheet 12 can prevent a leakage of the fluid absorbed in the absorbent core 2 to the outside. The back sheet 12 forms the major portion of the outer surface of the sanitary product 1 when it is worn by the wearer, and thus prevents a soiling of bed linen or underwear.

The absorbent core 2 placed between the back sheet 12 and the acquisition-distribution layer 11 provides the major portion of the absorption capacity of the sanitary product 1. The absorption matrix 3 of the absorbent core 2 encapsulated by the absorbent core cover 4 comprises, as fluid-absorbing particles, a large proportion of super-absorbing particles (SAP) as well as further absorbing particles, such as cellulose, synthetic fibres and gelling materials. The proportion of super-absorbing particles can be at least 50%, e.g., at least 80%, and optionally up to 100% of the total weight of the absorbing particles of the absorption matrix 3. This permits, compared to conventional absorbent cores having a high proportion of cellulose particles, a relatively thin inventive absorbent core 2, which permits, apart from an increased fluid acquisition, an improved fit and a better wearing comfort of the sanitary product 1.

The top sheet 10 and the back sheet 12, as well as optionally also the acquisition-distribution layer 11, could be connected to the absorbent core cover 4 at the edge 7 of the absorbent core 2 to safely position the absorbent core 2 within the sanitary product 1.

Figure 4:
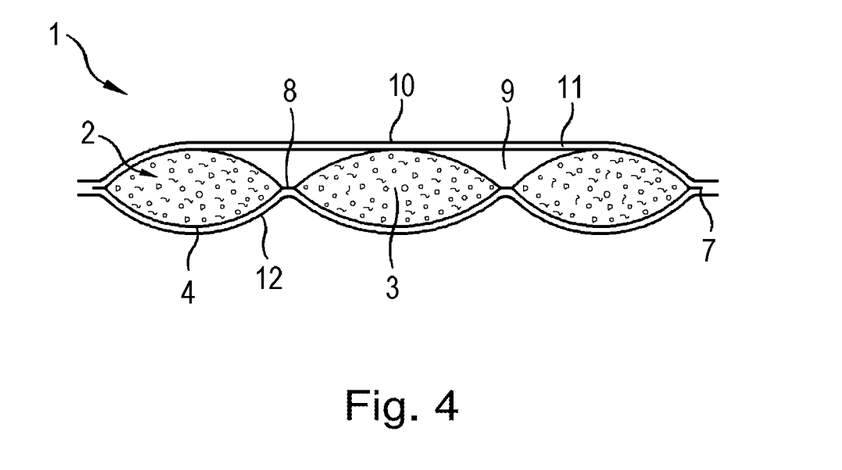
FIG. 4 shows a section through the sanitary product of FIG. 3 in an at least partially swelled state.

FIG. 4 shows the sanitary product 1 described in FIG. 3 in a state where the absorption matrix 3 has already swelled at least partially by already acquired fluid. In this at least partially swelled state of the absorption matrix 3, between the upper side sheet 5 of the absorbent core cover 4 and the acquisition-distribution layer 11, large channels 9 are formed via which the body fluids entered into the sanitary product 1 can be quickly transported to other regions of the absorbent core 2 to be absorbed there by the absorption matrix 3 of the absorbent core 2. In contrast to conventional absorbent cores, where in a lateral lying position of the wearer, the unbound fluid in the channels can lead to a leakage of the sanitary product due to gravity, in an absorbent core 2 according to the invention, the unbound fluid in the channels 9 is quickly absorbed by the upper side sheet 5 of the absorbent core cover 4, despite a possible local gel blocking, stored, passed on in the upper side sheet 5, and then discharged to the absorption matrix 3 into an unblocked region of the absorption matrix 3.

Figure 5:
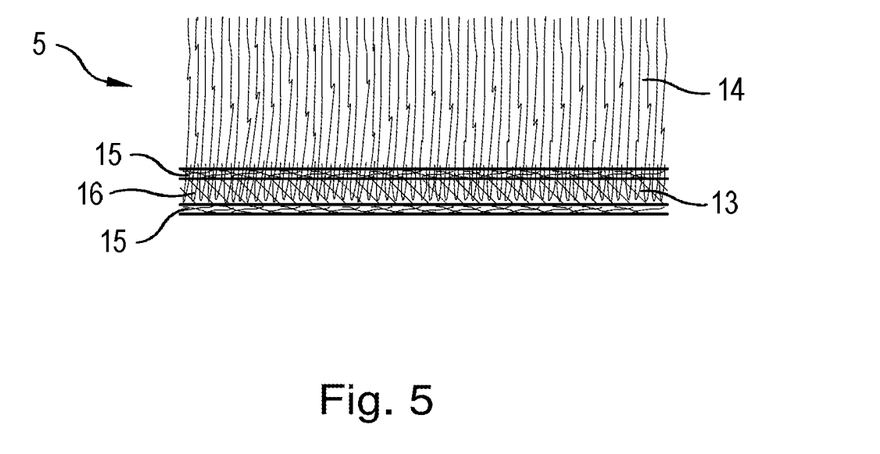
FIG. 5 shows a section through the upper layer of an absorbent core cover for an absorbent core according to FIG. 1 and FIG. 2.

FIG. 5 represents, by way of example, the structure of an upper side sheet 5 of the absorbent core cover 4. The upper side sheet 5 consists of a fleece composite with a fixing layer 13 and a transfer layer 14, the transfer layer 14 in an inventive sanitary product 1 according to FIG. 3 and FIG. 4 facing the acquisition-distribution layer 11, and the fixing layer 13 facing the absorption matrix 3 of the absorbent core 2. In some embodiments, the fixing layer 13 is embodied as an SMS fleece with a typical SMS layer structure, in which between two spunbonds 15, a meltblown fleece 16 is arranged and connected to the spunbonds 15 by calendar bonding. This fixing layer 13 has a low permeability and therefore essentially serves to retain the particles of the absorption matrix 3 within the absorbent core 2. As an alternative, this fixing layer 13 can also be embodied of a simple spunbond 15 or a simple meltblown fleece 16, whereby a somewhat simpler structure of the upper side sheet 5 with a single-layer fixing layer 13 is achieved, if an altogether low permeability of the upper side sheet 5 is achieved in connection with the transfer layer 14. In contrast, the transfer layer 14 connected to the fixing layer 13 serves to absorb free fluid as quickly as possible, to distribute and intermediately store it in the transfer layer 14, and to discharge it to the absorption matrix 3 via the fixing layer 13. In some embodiments, the transfer layer 14 embodied as a staple fibre fleece is needled into the fixing layer 13, whereby interface effects at the upper spunbond 15 of the fixing layer 13 are minimized, and the fluid transfer from the transfer layer 14 into the fixing layer 13, and finally into the absorption matrix 3, can be improved.

Below, various embodiments of the upper side sheet 5 of the absorbent core cover 4 for an inventive absorbent core 2 will be illustrated more in detail and their properties described. For comparison reasons, an SMS fleece employed for conventional absorbent core covers is also specified.

Besides the SMS fleece according to prior art specified for comparison purposes, the structure of five different composite fleeces for the upper side sheet 5 of the absorbent core cover 4 of an absorbent core 2 according to the invention will be described in the following table.

TABLE 1

Structure of the composite fleeces employed in the tests.

| Fleece No. | Designation | Fixing layer | Transfer layer |
|---|---|---|---|
| 1 | Comparative fleece | SMS fleece of polypropylene, 8 g/m² | — |
| 2 | Fine fibre mixture 1 | SMS fleece of polypropylene, 8 g/m² | Staple fibre fleece of viscose 1.7 dtex, 22 g/m² |
| 3 | Fine fibre mixture 2 | SMS fleece of polypropylene, 8 g/m² | Staple fibre fleece of viscose 1.7 dtex, 47 g/m² |
| 4 | Coarse fibre mixture 1 | SMS fleece of polypropylene, 8 g/m² | Staple fibre fleece of 40% of polyester 10 dtex, 40% of polyester/copolyester 4.4 dtex, 20% of viscose 1.7 dtex, 60 g/m² |
|   | Coarse fibre mixture 2 | SMS fleece of polypropylene, 8 g/m² | Staple fibre fleece of 40% of polyester 10 dtex, 32.5% of polyester/copolyester 4.4 dtex, 27.5% of viscose 1.7 dtex, 60 g/m² |
| 6 | gradual mixture | SMS fleece of polypropylene, 8 g/m² | Staple fibre fleece of coarse fibre with 60% of polyester, 3.3 dtex, 15% of polyester/copolyester 4.4 dtex, 25% of viscose 1.7 dtex, and fine fibre of viscose 1.7 dtex, 60 g/m² |

To evaluate the properties of the various composite fleeces and the comparative fleece from prior art for the use as an upper side sheet 5 of the absorbent core cover 4 of an absorbent core 2 according to the invention, the fleeces were subjected to various tests which will be described in detail below.

Maximum Water Acquisition

The maximum water acquisition expresses which amount of fluid can be absorbed by one of the fleeces stated above without compressive load. By indicating the maximum water acquisition in percent and in grams per gram of the fleece, the capacity of a material to immobilize free liquid can be described. To be able to better assess which amount of fluid per area of the employed upper side layer can be absorbed, a conversion to the absorbed fluid in millimeters based on one square meter of fleece is recommended.

According to the intended application as an upper side sheet 5 of an absorbent core cover 4, a high water acquisition is advantageous since the fleece then has the property of immobilising larger amounts of fluids.

TABLE 2

Maximum water acquisition in percent, in gram per gram of fleece, and in millilitres per square metre of fleece.

| Fleece No. | Max. WA [%] | Max. WA [g/g] | Max. WA [ml/m²] |
|---|---|---|---|
| 1 | 57 | 0.57 | 4,56 |
| 2 | 1110 | 11.10 | 333 |
| 3 | 742 | 7.42 | 482.3 |
| 4 | 1180 | 11.80 | 708 |
| 5 | 808 | 8.08 | 633.6 |
| 6 | 1056 | 10.56 | 404 |

Run-Off

The performed run-off test is based on the standard WSP 80.9 of the EDANA (European Disposables and Nonwovens Association). In the process, 25 ml of a 0.9% NaCl solution are applied onto an inclined fleece within 4+/−0.1 seconds. In contrast to the standard WSP 80.9, for this test, the fleece was inclined at an angle of 30° instead of 25°.

The run-off test gives an indication about the capacity of a material to pass-on a defined amount of urine substitute fluid to the underlying layer, while the experimental arrangement simulates an inclined position of a sanitary product 1. The lower the percentage value is, the better is the acquisition and the passing-on of the fluid into the material and into the underlying absorption matrix 3 of the absorbent core 2. In addition, the absolute amount of the unabsorbed fluid (run-offs) is indicated in millimeters. Here, one can say that the higher the absolute amount of the run-off is, the fewer fluid is absorbed by the fleece and the underlying absorbent core 2. This is to be rated as negative since unbound fluid in a sanitary pad 1 can lead to a leakage of the sanitary product 1 due to the free movement in the channels 9, representing a quality defect.

The quantities "run-off acquisition paper" and "run-off acquisition fleece" show whether the acquired fluid is stored, directly upon absorption, to a greater extent in the fleece or to a greater extent in the absorbent core 2. By tendency, it is advantageous if more fluid is stored in the paper, that means in the absorbent core 2, because the fluid is to be finally stored therein. This additionally reduces the probability of a rewetting of the sanitary product 1.

In modern constructions of sanitary products 1 with fluid channels 9 (e.g., Channel Core Products), an immediate fluid acquisition is not always given. At the point of the fluid penetration at the absorbent core 2, a so-called gel blocking can occur. In the process, the super-absorbing particles of the absorption matrix 3 swell at this location to such an extent that no further fluid can be acquired. Therefore, an in-situ acquisition by the examined fleece can absolutely be considered as advantageous for minimizing the amount of the free, unbound fluid in the fluid channels 9.

The fine fibre mixtures, the fleeces with fleece numbers 2 and 3, have a high acquisition, while the coarse fibre mixtures, the fleeces with fleece numbers 4 and 5, are characterized by a direct passing-on of the fluid. A heterogeneous fleece structure, such as the gradual mixture with coarse fibres and fine fibres, the fleece with fleece number 6, combines the advantages of the other two solution approaches for a fleece composite of an upper side sheet 5 of an absorbent core cover 4.

TABLE 3

Run-off data with 25 ml of a 0.9% NaCl solution in % and ml, and fluid acquisition.

| Fleece No. | Run-off [%] | Run-off [ml] | Run-off acquisition paper [ml] | Run-off acquisition fleece [ml] |
|---|---|---|---|---|
| 1 | 0.3 | 0.1 | 24.8 | 0.04 |
| 2 | 41.21 | 10.3 | 8.06 | 2.3 |
| 3 | 23.36 | 5.8 | 9.51 | 6.1 |
| 4 | 0 | 0 | 21.42 | 0.7 |
| 5 | 0 | 0 | 21.27 | 3.07 |
| 6 | 43.48 | 10.87 | 3.69 | 8.32 |

Wicking

By wicking or the capillary rises of water, the soaking behavior of fluids against gravity invoked by capillary forces in the fleece are examined. The capillary channels are formed by the staple fibres in the fleece. Depending on the wetting properties of the fibre surface and the size of the capillaries, the capillary forces are differing.

The higher the measured capillary rise of water is, the higher are the capillary forces and the corresponding wicking in the fleece composite. By this, one can draw conclusions about the fluid distribution in the fleece.

TABLE 4

Capillary rises of water after 300 seconds.

| Fleece No. | Wicking after 300 seconds [mm] |
|---|---|
| 1 | 0 |
| 2 | 64.5 |
| 3 | 139 |
| 4 | 21 |
| 5 | 19.5 |
| 6 | 104 |

Strike Through

In the strike-through test, a defined amount of fluid is selectively introduced into the fleece, and the time, until the amount of fluid has been acquired by the fleece, is measured. For the application of a fleece in the field of fluid management, one can say that the shorter the strike-through time is, the better the fleece functions, i. e. the transport of the fluid through the upper side sheet 5 of the absorbent core cover 4.

TABLE 5

Data for a triple strike-through test.

| Fleece No. | Strike Through [s] |
|---|---|
| 1 | 1.6/2.4/2.2 |
| 2 | 2.3/2.6/2.6 |
| 3 | 2.9/2.6/3.5 |
| 4 | 0.86/1.08/1.25 |
| 5 | 0.72/1.38/1.4 |
| 6 | 1.14/1.89/2 |

Air Permeability

By measuring the air permeability in l/m²/s at a test pressure of 200 Pa it is tested which amount of air flows through the fleece within one second, based on one square meter of fleece. Fleece fabrics having a higher fine fibre proportion have a lower air permeability than fleece fabrics having a higher coarse fibre proportion. This can be explained by the fact that fleeces with finer fibres have a greater inner surface than fleeces with coarser fibres. Via the parameter of the air permeability, thus comparisons between different fleece fabrics in view of their tightness can be made. To prevent in particular, the super-absorbing particles of the absorption matrix 3 from penetrating through the fleece for the absorbent core cover 4 and exiting from the absorbent core 2, the absorbent core cover 4 has to comprise a certain tightness, usually at least 3,500 l/m²/s.

TABLE 6

Data of the air permeability for assessing the tightness of the fleece fabrics.

| Fleece No. | Air permeability [l/m²/s] at 200 Pa |
|---|---|
| 1 | 3200 |
| 2 | 3353 |
| 3 | 1713 |
| 4 | 5300 without SMS fleece |
|   | 2590 with SMS fleece |
| 5 | 4915 without SMS fleece |
|   | 2410 with SMS fleece |
| 6 | 3000 without SMS fleece |
|   | 2010 with SMS fleece |

For assessing the total air permeability of multilayer fleeces with different tightness degrees of the individual layers, a calculation on the basis of the air permeability of the individual fleeces can be performed. The multiplication inverse of the total air permeability is determined by an addition of the multiplication inverse of the air permeabilities of the individual layers.

Pore Volumes

The relative porosity ε of the fleece fabrics employed in the tests result from the pore volume of the fleeces which can be calculated by the following formula:

$$\varepsilon = 100 * \left(1 - \frac{FG}{e * \rho_{Faser}}\right)$$

Here, FG is the grammage in g/m², e is the thickness of the fleece fabric in μm, and $\rho_{Faser}$ is the relative density of the fibre in g/cm³.

The total pore volume can be correspondingly determined by the following formula:

$$V_0 = \varepsilon * V_{material}$$

TABLE 7

Calculated pore volume.

| Fleece No. | Grammage [g/m²] | Thickness [mm] | Fibre material | Fineness [dtex] | Proportion | Pore volume |
|---|---|---|---|---|---|---|
| 1 | 8 | 0.14 | PP | 1.3 | 100% | 0.940 |
| 2 | 30 | 0.49 | PP | 1.3 | 27% | 0.953 |
|   |   |   | CV | 1.7 | 73% |   |
| 3 | 55 | 0.63 | PP | 1.3 | 14.5% | 0.956 |
|   |   |   | CV | 1.7 | 85.5% |   |
| 4 | 68 | 1.0 | PET | 10 | 35% | 0.949 |
|   |   |   | CV | 1.7 | 18% |   |
|   |   |   | CoPET | 4.4 | 35% |   |
|   |   |   | PP | 1.3 | 12% |   |
| 5 | 68 | 1.19 | PET | 10 | 35% | 0.957 |
|   |   |   | CV | 1.7 | 24% |   |
|   |   |   | CoPET | 4.4 | 29% |   |
|   |   |   | PP | 1.3 | 12% |   |
| 6 | 68 | 0.79 | PET | 3.3 | 35% | 0.937 |
|   |   |   | CV | 1.7 | 44% |   |
|   |   |   | CoPET | 4.4 | 9% |   |
|   |   |   | PP | 1.3 | 12% |   |

Free Volume and Fibre Surface

By the free volume in the fleece, conclusions can be drawn about the existing porosity of the respective composite fleeces. The free volume in the fleece offers the possibility of storing liquid. This means, the higher the free volume in the fleece is, the more liquid can be bound in the fleece. Here, via the size of the fibre surface in the fleece fabric, a distinction can also be made between the fine fibre fleeces and the coarse fibre fleeces of the composite fleeces employed in the tests. The indications of the free volume in the fleece and the fibre surface in the fleece each relate to one square meter of fleece.

TABLE 8

Calculated values of the free volume in the fleece and the fibre surface in the fleece

| Fleece No. | Free volume [mm³] | Fibre surface [m²] |
|---|---|---|
| 1 | 131672 | 8.6 |
| 2 | 467279 | 22.1 |
| 3 | 590923 | 27.1 |
| 4 | 1080881 | 17.2 |
| 5 | 1131150 | 16.4 |
| 6 | 768982 | 12.2 |

Results

It becomes clear from the results of the test that there are three different possibilities of designing the staple fibre fleece for the transfer layer 14 of a composite fleece at least employed as an upper side sheet 5 of the absorbent core cover 4. The fleece fabrics employed in the tests each consist of a fixing layer 13 of a pre-solidified SMS fleece and a different transfer layer 14 of a staple fibre fleece needled into it. For the different transfer layers 14, the following classification can be made:

1. Fine fibre structures (<3.3 dtex) with a high proportion of cellulosic fibre (50-100%).
2. Coarse fibre structures (>3.3 dtex to 12.0 dtex) with a moderate proportion of cellulosic fibre (15-20%).
3. Combination of coarse fibre structure and fine fibre structure.

In the inventive embodiment of an absorbent core 2 for sanitary products 1, apart from the acquisition of the fluid by the absorbent core cover 3, above all a transfer and a distribution of the fluid towards the absorption matrix 4 of the absorbent core 2 are also desired. Compared to prior art (fleece number 1), the improved capillarity of the composite fleeces (fleece numbers 2 to 6) is of assistance here.

By the incorporation of the staple fibres in the transfer layer 14 into the fixing layer 13 of the composite fleeces, the interface effects at the fixing layer 13, in particular with an SMS fleece, are minimized, and the fluid transfer from the transfer layer 13 to the absorption matrix 14 functions in a better way. This can, in particular, be explained by the so-called wicking since the staple fibres of the transfer layer 14 penetrate through the fixing layer 13 in the z-direction (perpendicular to the upper side sheet 5), and capillary channels are formed through which fluids can be more easily transported into the absorption matrix 4 of the absorbent core 2.

Evaluation

A mere fixing layer (fleece number 1), as it is employed in prior art as upper side sheet 5 and bottom side sheet 6 of an absorbent core cover exhibits insufficient properties of the relevant parameters for describing the liquid absorption and storage. Fleece number 1 does not have any absorption property (wicking) against gravity. In the run-off, too, there are deficiencies in the intermediate storage of fluid in the fleece. Taking the property of the maximum water acquisition into consideration, it becomes clear that this very flat and lightweight fleece with very fine fibres only has a very restricted capacity of acquiring fluids as an absorbent core cover 4.

Fleece number 2, in contrast, has a highly improved fluid absorption and fluid storage as is confirmed by the static test of the maximum water acquisition with a value of more than 1100%. If the fluid is dynamically applied onto fleece number 2, as is the case in the run-off test, this fleece composite supplies a significant acquisition of the applied amount of fluid of more than 50% of the total volume. Here, fleece number 2 passes on the major part of the absorbed amount of fluid into the underlying layer, i. e. the absorption matrix 3 of the absorbent core 2.

The same as for fleece number 2 applies to fleece number 3. By the higher grammage, the maximum water acquisition in milliliters per square meter is very high in this fleece composite, whereby fleece number 3 is in a position to acquire large amounts of fluid. Even in the dynamic application of the fluid in the run-off test, this fleece number 3 performances very well since more than 75% of the applied amount of fluid are absorbed.

In fleece number 4, the coarse fibre structure offers a high free volume per $m^2$ of the fleece surface, whereby temporarily, a very high maximum water acquisition is achieved. By the reduced proportion of cellulosic fibres, in the run-off test, the total amount of applied fluid can be absorbed, only a very small portion of the absorbed amount of fluid remaining in the fleece. The absorbed amount of fluid is essentially passed on directly and nearly completely into the underlying layer, i. e. the absorption matrix 3. In the run-off test, fleece number 4 achieves the best result of all examined fleece structures.

For fleece number 5, similar to fleece number 4, the coarse fibre structure also offers a high free volume and a very high maximum water acquisition per $m^2$ of the fleece surface. In the run-off test, again the total amount of fluid is acquired, however, a smaller proportion of the fluid is absorbed in the fleece and not immediately passed on to the underlying layer.

Fleece number 6 is a combination of a coarse fibre layer and a fine fibre layer of staple fibres, whereby a high fluid absorption is achieved at the transfer layer 14, the surface facing the body of a wearer. Here, fleece number 6 provides a particularly high proportion of porosity which can be utilized for the fluid acquisition. The fine fibre layer facing the fixing layer 13 and finally the absorption matrix 4 of the absorbent core 2, supports, by higher capillary forces, the good dewatering by the transfer layer 14, resulting in a large-surface distribution of the fluid in fleece number 6.

LIST OF REFERENCE NUMERALS

1 sanitary product
2 absorbent core
3 absorption matrix
4 absorbent core cover
5 upper side sheet
6 bottom side sheet
7 edge
8 connection region
9 channel
10 top sheet
11 acquisition-distribution layer
12 back sheet
13 fixing layer
14 transfer layer
15 spunbond
16 meltblown fleece

What is claimed is:

1. An absorbent core for sanitary products, comprising an absorption matrix having a high proportion of super-absorbing particles and an absorbent core cover for enveloping the absorption matrix,
   wherein the absorbent core cover comprises at least one upper side sheet and at least one bottom side sheet, and the absorbent core cover comprises at least one connection region spaced apart from the edge of the absorbent core in which the upper side sheet and the bottom side sheet are connected to each other,
   wherein at least the upper side sheet of the absorbent core cover is embodied as a fleece composite with a fixing layer with a low permeability to retain the particles in the absorption matrix, and a transfer layer for acquiring fluid,
   wherein the fixing layer is embodied as a spunbond fleece, a meltblown fleece, or an SMS fleece with an SMS layer structure, and the transfer layer is embodied as a staple fibre fleece, and
   wherein the staple fibres of the staple fibre fleece comprise coarse fibres with fibre finenesses within a range of 3.3 to 12.0 dtex and a coarse fibre cellulosic fibre proportion of up to 45%.

2. The absorbent core for sanitary products of claim 1, wherein the staple fibres of the staple fibre fleece further comprise fine fibres with fibre finenesses within a range of 1.0 to 3.3 dtex and a fine fibre cellulosic fibre proportion of 50% to 100%.

3. The absorbent core for sanitary products of claim 2, wherein the fine fibres have a fibre fineness within a range of 1.3 to 2.2 dtex.

4. The absorbent core for sanitary products of claim 2, wherein the coarse fibre cellulosic fibre proportion is between 15% and 20%.

5. The absorbent core for sanitary products of claim 1, wherein the coarse fiber cellulosic fibre proportion is between 15% and 20%.

6. The absorbent core for sanitary products of claim 1, wherein the staple fibre fleece is manufactured by means of a spunlace process.

7. The absorbent core for sanitary products of claim 1, wherein the staple fibre fleece is needled into the fixing fleece.

8. The absorbent core for sanitary products of claim 1, wherein at least the upper side sheet of the absorbent core cover has a thickness of greater than 0.35 mm.

9. The absorbent core for sanitary products of claim 8, wherein the thickness is between 0.5 mm and 1.2 mm.

10. The absorbent core for sanitary products of claim 1, wherein at least the upper side sheet of the absorbent core cover comprises, at a test pressure of 200 Pa, an air permeability of maximally 3,500 $l/m^2/s$.

11. The absorbent core for sanitary products of claim 10, wherein the air permeability is maximally 3,000 $l/m^2/s$.

12. The absorbent core for sanitary products of claim 1, wherein at least the upper side sheet of the absorbent core cover comprises, in a wicking test, a capillary rise of water of at least 10 mm after 300 seconds.

13. The absorbent core for sanitary products of claim 1, wherein a run-off proportion is, at least for the upper side sheet of the absorbent core cover, smaller than 50% in a run-off test based on WSP 80.9.

14. The absorbent core for sanitary products of claim 1, wherein the strike-through time for at least the upper side sheet of the absorbent core cover is less than 3 seconds in a strike-through test.

15. The absorbent core for sanitary products of claim 14, wherein the strike-through time is less than 1.5 seconds.

16. A sanitary product with an optional top sheet, an acquisition-distribution layer (ADL), an absorbent core for sanitary products according to claim 1, and an optional back sheet, wherein the upper side sheet and the bottom side sheet are connected to each other to form a channel opposite the acquisition-distribution layer, when the absorption matrix swells by acquisition of fluid.

17. A method for manufacturing an absorbent core for sanitary products, the method comprising:
   providing the absorbent core of claim 1,
   forming the absorbent core cover by affixing the at least one upper side sheet and the at least one bottom side sheet through the at least one connection region; and
   applying the absorbent core cover to the absorption matrix such that the absorbent core cover envelopes the absorption matrix.

18. The method of claim 17, further comprising needling the transfer layer into the fixing layer.

* * * * *